US006282447B1

(12) United States Patent
Cook et al.

(10) Patent No.: US 6,282,447 B1
(45) Date of Patent: Aug. 28, 2001

(54) CARDIAC STIMULATOR WITH RATE-ADAPTIVE PVARP

(75) Inventors: Douglas Jason Cook, Minnetonka, MN (US); Randolph K. Armstrong, Missouri City, TX (US); Joseph W. Vandegriff, Brazoria, TX (US); Denise R. Brown, Bellaire, TX (US)

(73) Assignee: Intermedics Inc., Angleton, TX (US)

( * ) Notice: Subject to any disclaimer, the term of this patent is extended or adjusted under 35 U.S.C. 154(b) by 0 days.

(21) Appl. No.: 09/376,024

(22) Filed: Aug. 19, 1999

(51) Int. Cl.⁷ .................................................. A61N 1/362
(52) U.S. Cl. .................................................. 607/9; 607/25
(58) Field of Search .................................... 607/9, 25

(56) References Cited

U.S. PATENT DOCUMENTS

| 4,390,022 | 6/1983 | Calfee et al. ................... 128/419 |
| 4,401,119 | 8/1983 | Herpers ..................... 128/419 PG |
| 4,404,972 | 9/1983 | Gordon et al. ............. 128/419 PG |
| 4,539,992 | 9/1985 | Calfee et al. ................... 128/419 |
| 4,572,193 | 2/1986 | Mann et al. ..................... 128/419 |
| 5,074,308 | * 12/1991 | Sholder et al. ................. 128/697 |
| 5,086,774 | 2/1992 | Duncan ........................... 128/419 |
| 5,097,832 | 3/1992 | Buchanan ....................... 128/419 |
| 5,129,393 | 7/1992 | Brumwell ................... 128/419 PG |
| 5,144,949 | 9/1992 | Olson ........................ 128/419 PG |
| 5,273,035 | 12/1993 | Markowitz et al. ............... 607/14 |
| 5,496,350 | * 3/1996 | Lu .................................... 607/14 |
| 5,507,783 | * 4/1996 | Buchanan .......................... 607/14 |
| 5,522,859 | 6/1996 | Stroebel et al. ................... 607/19 |
| 5,540,725 | 7/1996 | Bornzin et al. ..................... 607/9 |
| 5,601,615 | 2/1997 | Markowitz et al. ................ 607/28 |
| 5,609,614 | 3/1997 | Stotts et al. ...................... 607/29 |
| 5,626,623 | 5/1997 | Kieval et al. ...................... 607/23 |
| 5,674,255 | 10/1997 | Walmsley et al. ................ 607/14 |
| 5,674,257 | 10/1997 | Stroebel et al. ................... 607/17 |
| 5,792,183 | 8/1998 | Esler ................................. 607/4 |
| 5,861,009 | 1/1999 | Randolph et al. ................ 607/17 |
| 5,861,012 | 1/1999 | Stroebel ............................ 607/28 |
| 5,954,755 | 9/1999 | Casavant ........................... 607/28 |

FOREIGN PATENT DOCUMENTS

96/15828   5/1996  (WO).

* cited by examiner

Primary Examiner—Carl Layno
(74) Attorney, Agent, or Firm—Schwegman, Lundberg, Woessner & Kluth, P.A.

(57) ABSTRACT

It has been determined that certain cardiac stimulators may operate in a manner in which the ventricular pace refractory period (VPRP) may be greater than the post-ventricular atrial refractory period (PVARP). Various exemplary techniques may be used to improve the ability of cardiac stimulators to lengthen the PVARP. In accordance with one technique, the VPRP is adjusted with the pacing rate so that as the pacing rate becomes slower the VPRP increases. The VPRP is compared with the PVARP. The PVARP remains constant until the VPRP becomes greater than the PVARP. Then, the PVARP is adjusted to make it greater than or equal to the VPRP. In accordance with another technique, the VPRP and the PVARP are adjusted with the pacing rate, with the PVARP remaining greater than or equal to the VPRP.

54 Claims, 6 Drawing Sheets

CARDIAC STIMULATOR WITH RATE-ADAPTIVE PVARP

BACKGROUND OF THE INVENTION

1. Field of the Invention

The present invention relates generally to cardiac stimulators and, more particularly, to dual-chamber cardiac stimulators that have an improved ability to detect tachyarrhythmias.

2. Description of the Related Art

This section is intended to introduce the reader to various aspects of art which may be related to various aspects of the present invention which are described and/or claimed below. This discussion is believed to be helpful in providing the reader with background information to facilitate a better understanding of the various aspects of the present invention. Accordingly, it should be understood that these statements are to be read in this light, and not as admissions of prior art.

As most people are aware, the human heart is an organ having four chambers. A septum divides the heart in half, with each half having two chambers. The upper chambers are referred to as the left and right atria, and the lower chambers are referred to as the left and right ventricles. Deoxygenated blood enters the right atrium through the vena cava. Contraction of the right atrium and of the right ventricle pump the deoxygenated blood through the pulmonary arteries to the lungs where the blood is oxygenated. This oxygenated blood is carried to the left atrium by the pulmonary veins. From this cavity, the oxygenated blood passes to the left ventricle and is pumped to a large artery, the aorta, which delivers the blood to the other portions of the body through the various branches of the vascular system.

In the normal human heart, the sinus node (generally located near the junction of the superior vena cava and the right atrium) constitutes the primary natural pacemaker by which rhythmic electrical excitation is developed. The cardiac impulse arising from the sinus node is transmitted to the two atrial chambers. In response to this excitation, the atria contract, pumping blood from those chambers into the respective ventricles. The impulse is transmitted to the ventricles through the atrioventricular (AV) node to cause the ventricles to contract. This action is repeated in a rhythmic cardiac cycle in which the atrial and ventricular chambers alternately contract and pump, then relax and fill. One-way valves between the atrial and ventricular chambers in the right and left sides of the heart and at the exits of the right and left ventricles prevent backflow of the blood as it moves through the heart and the circulatory system.

The sinus node is spontaneously rhythmic, and the cardiac rhythm originating from the sinus node is referred to as sinus rhythm. This capacity to produce spontaneous cardiac impulses is called rhythmicity. Some other cardiac tissues also possess this electrophysiologic property and, hence, constitute secondary natural pacemakers. However, the sinus node is the primary pacemaker because it has the fastest spontaneous rate and because the secondary pacemakers tend to be inhibited by the more rapid rate at which impulses are generated by the sinus node.

The resting rates at which sinus rhythm occurs in normal people differ from age group to age group, generally ranging between 110 and 150 beats per minute ("bpm") at birth, and gradually slowing in childhood to the range between 65 and 85 bpm usually found in adults. The resting sinus rate, typically referred to simply as the "sinus rate," varies from one person to another and, despite the aforementioned usual adult range, is generally considered to lie anywhere between 60 and 100 bpm (the "sinus rate range") for the adult population.

A number of factors may affect the sinus rate, and some of those factors may slow or accelerate the rate sufficiently to take it outside of the sinus rate range. Slow rates (below 60 bpm) are referred to as sinus bradycardia, and high rates (above 100 bpm) are referred to as sinus tachycardia. In particular, sinus tachycardia observed in healthy people arises from various factors which may include physical or emotional stress, such as exercise or excitement, consumption of beverages containing alcohol or caffeine, cigarette smoking, and the ingestion of certain drugs. The sinus tachycardia rate usually ranges between 101 and 160 bpm in adults, but has been observed at rates up to (and in infrequent instances, exceeding) 200 bpm in younger persons during strenuous exercise.

Sinus tachycardia is sometimes categorized as a cardiac arrhythmia, since it is a variation from the normal sinus rate range. Arrhythmia rates which exceed the upper end of the sinus rate range are termed tachyarrhythmias. Healthy people usually experience a gradual return to their normal sinus rate after the removal of the factors giving rise to sinus tachycardia. However, people suffering from disease may experience abnormal arrhythmias that may require special, and in some instances immediate, treatment. In this text, we typically refer to abnormally high rates that have not yet been determined to be caused by myocardial malfunction as tachycardias and to abnormally high rates that have been determined to be caused by myocardial malfunction as tachyarrhythmias.

It should also be appreciated that an abnormal tachyarrhythmia may initiate fibrillation. Fibrillation is a tachyarrhythmia characterized by the commencement of completely uncoordinated random contractions by sections of conductive cardiac tissue of the affected chamber, quickly resulting in a complete loss of synchronous contraction of the overall mass of tissue and a consequent loss of the blood-pumping capability of that chamber.

In addition to rhythmicity, other electrophysiologic properties of the heart include excitability and conductivity. Excitability, which is the property of cardiac tissue to respond to a stimulus, varies with the different periods of the cardiac cycle. As one example, the cardiac tissue is not able to respond to a stimulus during the absolute refractory phase of the refractory period, which is approximately the interval of contraction from the start of the QRS complex to the commencement of the T wave of the electrocardiogram. As another example, the cardiac tissue exhibits a lower than usual response during another portion of the refractory period constituting the initial part of the relative refractory phase, which is coincident with the T wave. Also, the excitability of the various portions of the cardiac tissue differs according to the degree of refractoriness of the tissue.

Similarly, the different portions of the heart vary significantly in conductivity, which is a related electrophysiologic property of cardiac tissue that determines the speed with which cardiac impulses are transmitted. For example, ventricular tissue and atrial tissue are more conductive than AV junction tissue. The longer refractory phase and slower conductivity of the AV junction tissue give it a significant natural protective function, as described in more detail later.

However, for a variety of reasons, a person's heart may not function properly and, thus, endanger the person's well-being. Most typically, heart disease affects the rhythmicity of the organ, but it may also affect the excitability and/or conductivity of the cardiac tissue as well. As most people are aware, medical devices have been developed to facilitate heart function in such situations. For instance, if a person's heart does not beat properly, a cardiac stimulator may be used to provide relief. A cardiac stimulator is a medical device that delivers electrical stimulation to a patient's heart. A cardiac stimulator generally includes a pulse generator for creating electrical stimulation pulses and a conductive lead for delivering these electrical stimulation pulses to the designated portion of the heart. As described in more detail below, cardiac stimulators generally supply electrical pulses to the heart to keep the heart beating at a desired rate, although they may supply a relatively larger electrical pulse to the heart to help the heart recover from fibrillation.

Early pacemakers were devised to treat bradycardia. These pacemakers did not monitor the condition of the heart. Rather, early pacemakers simply provided stimulation pulses at a fixed rate and, thus, kept the heart beating at that fixed rate. However, it was found that pacemakers of this type used an inordinate amount of energy due to the constant pulse production. Even the sinus node of a heart in need of a pacemaker often provides suitable rhythmic stimulation occasionally. Accordingly, if a heart, even for a short period, is able to beat on its own, providing an electrical stimulation pulse using a pacemaker wastes the pacemaker's energy.

To address this problem, pacemakers were subsequently designed to monitor the heart and to provide stimulation pulses only when necessary. These pacemakers were referred to as "demand" pacemakers because they provided stimulation only when the heart demanded stimulation. If a demand pacemaker detected a natural heartbeat within a prescribed period of time, typically referred to as the "escape interval," the pacemaker provided no stimulation pulse. Because monitoring uses much less power than generating stimulation pulses, the demand pacemakers took a large step toward conserving the limited energy contained in the pacemaker's battery.

Clearly, the evolution of the pacemaker did not cease with the advent of monitoring capability. Indeed, the complexity of pacemakers has continued to increase in order to address the physiological needs of patients as well as the efficiency, longevity, and reliability of the pacemaker. For instance, even the early demand pacemakers provided stimulation pulses, when needed, at a fixed rate, such as 70 pulses per minute. To provide a more physiological response, pacemakers having a programmably selectable rate were developed. So long as the heart was beating above this programmnably selected rate, the pacemaker did not provide any stimulation pulses. However, if the heart rate fell below this programmably selected rate, the pacemaker sensed the condition and provided stimulation pulses as appropriate.

Another major step in adding complexity and functionality to pacemakers occurred with the advent of pacemakers that had dual chamber capability. Dual chamber pacemakers are capable of sensing and/or pacing in two chambers, typically the right atrium and right ventricle. Accordingly, the distal ends of an atrial lead and a ventricular lead are coupled to the dual chamber pacemaker. Typically, the proximal end of the atrial lead is threaded through the sub clavian vein and into the right atrium of the heart. Similarly, the proximal end of the ventricular lead is threaded through the sub clavian vein, through the right atrium, and into the right ventricle of the heart. Each lead includes a mechanism on its proximal end that attaches to the inner wall of the heart to establish the required electrical connection between the pacemaker and the heart. Dual chamber pacemakers, as compared to single chamber pacemakers, typically function in a more physiologically correct manner.

To provide even further physiological accuracy, pacemakers have now been developed that automatically change the rate at which the pacemaker provides stimulation pulses. These pacemakers are commonly referred to as "rate-responsive" pacemakers. Rate-responsive pacemakers sense a physiological parameter of the patient, or a non-physiological parameter such as activity, and alter the rate at which the stimulation pulses are provided to the heart. Typically, this monitored physiological parameter relates to the changing physiological needs of the patient. For instance, when a person is at rest, the person's heart need only beat relatively slowly to accommodate the person's physiological needs. Conversely, when a person is exercising, the person's heart tends to beat rather quickly to accommodate the person's heightened physiological needs.

Unfortunately, the heart of a person in need of a pacemaker may not be able to beat faster on its own. Prior to the development of rate-responsive pacemakers, patients were typically advised to avoid undue exercise, and pacemaker patients that engaged in exercise tended to tire quickly. Rate-responsive pacemakers help relieve this constraint by sensing one or more physiological or non-physiological parameters of a patient that indicates whether the heart should be beating slower or faster. If the pacemaker determines that the heart should be beating faster, the pacemaker adjusts its base rate upward to provide a faster pacing rate if the patient's heart is unable to beat faster on its own. Similarly, if the pacemaker determines that the patient's heart should be beating more slowly, the pacemaker adjusts its base rate downward to conserve energy and to conform the patient's heartbeat with the patient's less active state.

As noted above, pacemakers have historically been employed primarily for the treatment of heart rates which are unusually slow, i.e., bradyarrhythmias. However, over the past several years cardiac pacing has found significantly increasing usage in the management of heart rates which are unusually fast, i.e., tachyarrhythmias. Anti-tachyarrhythmia pacemakers take advantage of the previously mentioned inhibitory mechanism that acts on the secondary natural pacemakers to prevent their spontaneous rhymicity, sometimes termed "postdrive inhibition" or "overdrive inhibition." In essence, the heart may be stimulated with a faster than normal pacing rate (1) to suppress premature atrial or ventricular contractions that might otherwise initiate ventricular tachycardia, flutter (a tachyarrhythmia exceeding 200 bpm), or fibrillation or (2) to terminate an existing tachyarrhythmia.

Typically, these pulses need only be of sufficient magnitude to stimulate the excitable myocardial tissue in the immediate vicinity of the pacing electrode. However, another technique for terminating tachyarrhythmias, referred to as cardioversion, utilizes apparatus to shock the heart synchronized to the tachyarrhythmia with one or more current or voltage pulses of considerably higher energy content than that of the pacing pulses. Defibrillation, a related technique, also involves applying one or more high energy "countershocks" to the heart in an effort to overwhelm the chaotic contractions of individual tissue sections to allow reestablishment of an organized spreading of action potential from cell to cell of the myocardium and, thus, restore the synchronized contraction of the mass of tissue.

In the great majority of cases, atrial fibrillation is hemodynamically tolerated and not life-threatening because the atria provide only a relatively small portion (typically on the order of 15 to 20 percent) of the total volume of blood pumped by the heart per unit time, typically referred to as cardiac output. During atrial fibrillation, the atrial tissue remains healthy because it is continuing to receive a fresh supply of oxygenated blood as a result of the continued pumping action of the ventricles. Atrial tachyarrhythmia may also be hemodynamically tolerated because of the natural protective property of the junctional tissue attributable to its longer refractory period and slower conductivity than atrial tissue. This property renders the junctional tissue unable to respond fully to the more rapid atrial contractions. As a result, the ventricle may miss every other, or perhaps two of every three, contractions in the high rate atrial sequence, resulting in 2:1 or 3:1 A–V conduction and, thus, maintain relatively strong cardiac output and an almost normal rhythm.

In contrast to the atrial arrhythmias discussed above, cardiac output may be considerably diminished during an episode of ventricular tachyarrhythnia because the main pumping chambers of the heart, the ventricles, are only partially filled between the rapid contractions of those chambers. Moreover, ventricular tachyarrhythmia can present a risk of acceleration of the arrhythmia into ventricular fibrillation. As in the case atrial fibrillation, ventricular fibrillation is characterized by rapid, chaotic electrical and mechanical activity of the excitable myocardial tissue. However, in contrast to atrial fibrillation, ventricular fibrillation manifests an instantaneous cessation of cardiac output as the result of the ineffectual quivering of the ventricles—a condition that typically requires almost immediate treatment.

Due to the fact that the ventricles are responsible for the majority of cardiac output, it is common for cardiac stimulators to provide pacing pulses to the ventricle. Thus, most such cardiac stimulators follow the ventricular pacing pulse with a ventricular pace refractory period (VPRP). During this period, venticular activity is ignored by the cardiac stimulator to help prevent the misinterpretation of post-pace electrical activity (T-wave) as an event (R-wave) which could falsely inhibit the cardiac stimulator. Similarly, most cardiac stimulators follow a ventricular sense event with a corresponding ventricular sense refractory period (VSRP). The VPRP and VSRP are referred to herein generically as ventricular refractory periods (VRP), and, generally speaking, comments about one similarly apply to the other.

Early cardiac stimulators commonly used a fixed VRP, and many current dual-chamber and rate-responsive cardiac stimulators continue to use a fixed VRP. However, in the current rate-responsive cardiac stimulators, the VRP is limited by the maximum pacing rate so that it must be shorter than the shortest possible pacing interval. As a result, the fixed VRP may not be ideal for slower pacing rates that the cardiac stimulator is capable of delivering.

Some newer dual-chamber cardiac stimulators have begun to use a dynamically adaptive VPRP to reduce the length of the period as pacing rates increase and to lengthen the period as pacing rates decrease. However, after a venticular pace event, these newer dual-chamber cardiac stimulators will inhibit the tracking of atrial sense events during post-ventricular atrial refractory period (PVARP) to reduce the incidence of pacemaker-mediated tachycardia (PMT). Thus, a situation may exist where the VPRP may extend beyond the PVARP. In such a situation, an atrial event occurring after the PVARP will be tracked and a ventricular pacing pulse could be delivered prior to the end of the VPRP. This condition could lead to ventricular pacing during a vulnerable period in the ventricle.

In one technique, a minimum VPRP is used at the maximum pacing rate, a maximum VPRP is used at the minimum pacing rate, and the VPRP is linearly adjusted between these two limits based on the pacing rate. However, the PVARP is not addressed in this technique, and the above-mentioned problem could occur. Furthermore, if this problem is to be avoided using this technique, it must be done by restricting the limits. Given the potential variability in cardiac needs of patients, such restrictions would adversely affect the usefulness of the cardiac stimulator.

The present invention may address one or more of the matters set forth above.

SUMMARY OF THE INVENTION

Certain aspects commensurate in scope with the disclosed embodiments are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

In one exemplary embodiment, the VRP is adjusted with the pacing rate so that as the pacing rate becomes slower the VRP increases and vice versa. The VRP is compared with the PVARP. The PVARP remains constant until the VRP becomes greater than the PVARP. Then, the PVARP is adjusted to make it greater than or equal to the VRP. In accordance with another exemplary embodiment, the VRP and the PVARP are adjusted with the pacing rate, with the PVARP remaining greater than or equal to the VRP.

BRIEF DESCRIPTION OF THE DRAWINGS

The foregoing and other advantages of the invention will become apparent upon reading the following detailed description and upon reference to the drawings in which.

DETAILED DESCRIPTION OF SPECIFIC EMBODIMENTS

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Figure 1:
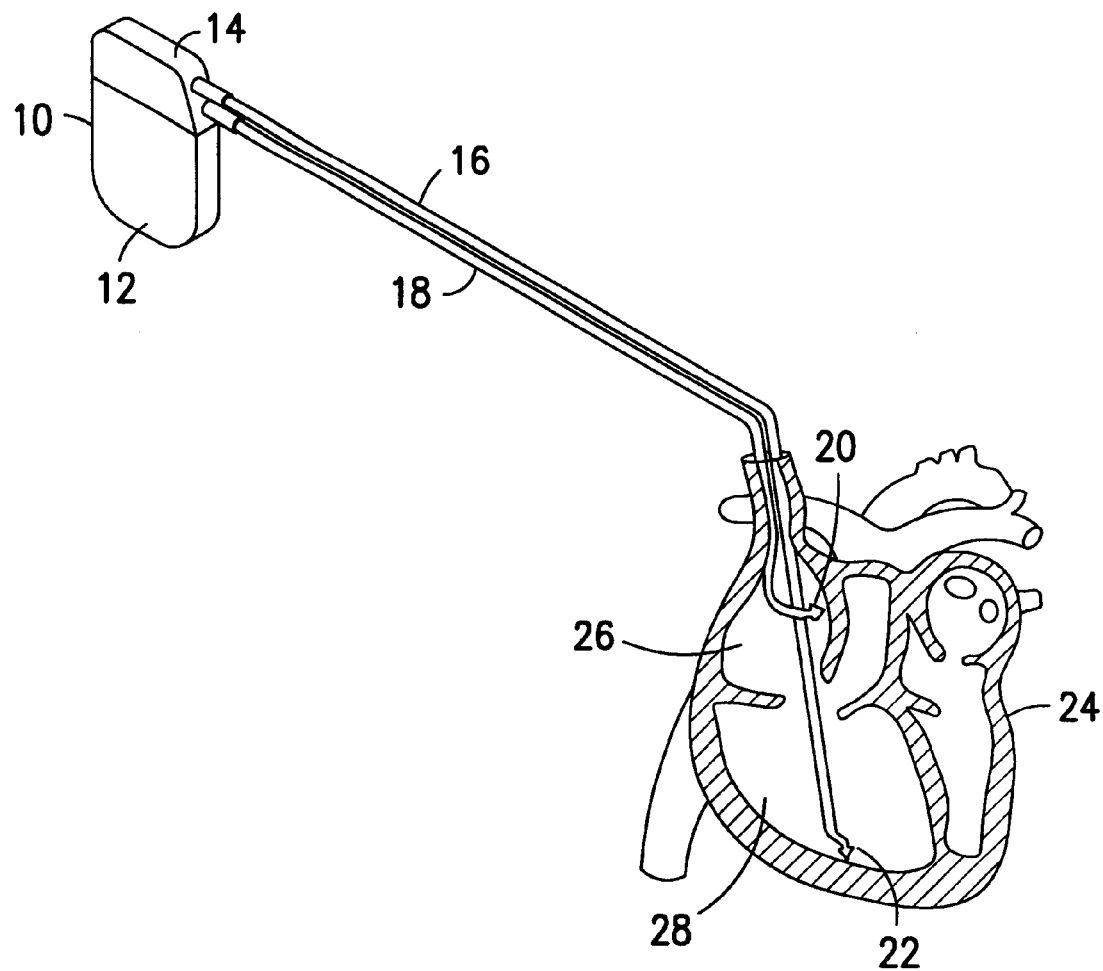
FIG. 1 illustrates a cardiac stimulator having two leads coupled to a patient's heart.

Turning now to the drawings, and referring initially to FIG. 1, one embodiment of a dual-chamber cardiac stimulator is illustrated and generally designated by the reference numeral 10. As discussed below, the cardiac stimulator 10 may include an apparatus for adjusting certain time intervals to reduce or prevent venticular pacing during a vulnerable period in the ventricle. The general structure and operation of the cardiac stimulator 10 will be discussed with respect to FIGS. 1 and 2. Then, various exemplary methods for adjusting certain ventricular time intervals will be described with reference to FIGS. 3–10. While the embodiments and methods are described below using the ventricular pace refractory period (VPRP) as an example, it should be understood that the embodiments and methods are believed to apply similarly to the ventricular sense refractory period (VSRP). These periods may be referred to generically as ventricular refractory periods (VRP).

One advantageous embodiment of the cardiac stimulator 10 may include the Res-Q 3D cardiac stimulator made by the present assignee, although the cardiac stimulator 10 may be embodied in a variety of ways, some of which are mentioned below, without departing from the scope of the present teachings. Indeed, other cardiac stimulators, whether conventional models or future models, may also benefit from the teachings set forth in this disclosure.

As shown in FIG. 1, the body of the cardiac stimulator 10 includes a case 12 and a header 14. The cardiac stimulator 10 may be implantable or non-implantable. If implantable, the case 12 and the header 14 are hermetically sealed to prevent bodily fluids from damaging the internal circuitry of the cardiac stimulator 10. Typically, the case 12 is made of titanium, and the header 14 is made of polyethylene.

In the described embodiment, the cardiac stimulator 10 is a dual chamber cardioverter/defibrillator (ICD), although it should be understood that the teachings set forth herein may apply to other types of cardiac stimulators. Because the cardiac stimulator 10 is a dual chamber ICD, it includes an atrial lead 16 and a ventricular lead 18. Typically, the leads 16 and 18 are generally flexible and include an electrically conductive core surrounded by a protective sheath. For instance, the internal core may be a coiled wire, and the protective sheath may be a coating of polyethylene.

Each lead 16 and 18 includes a respective tip 20 and 22 that is designed to be implanted or coupled to an interior surface of a chamber of the heart 24. As illustrated, the tip 20 of the atrial lead 16 is implanted in an inner wall of the right atrium 26 of the heart 24 for sensing and/or stimulating the right atrium 26. Similarly, the tip 22 of the ventricular lead 18 is implanted in an inner wall of the right ventricle 28 of the heart 24 for sensing and/or stimulating the right ventricle 28.

Figure 2:
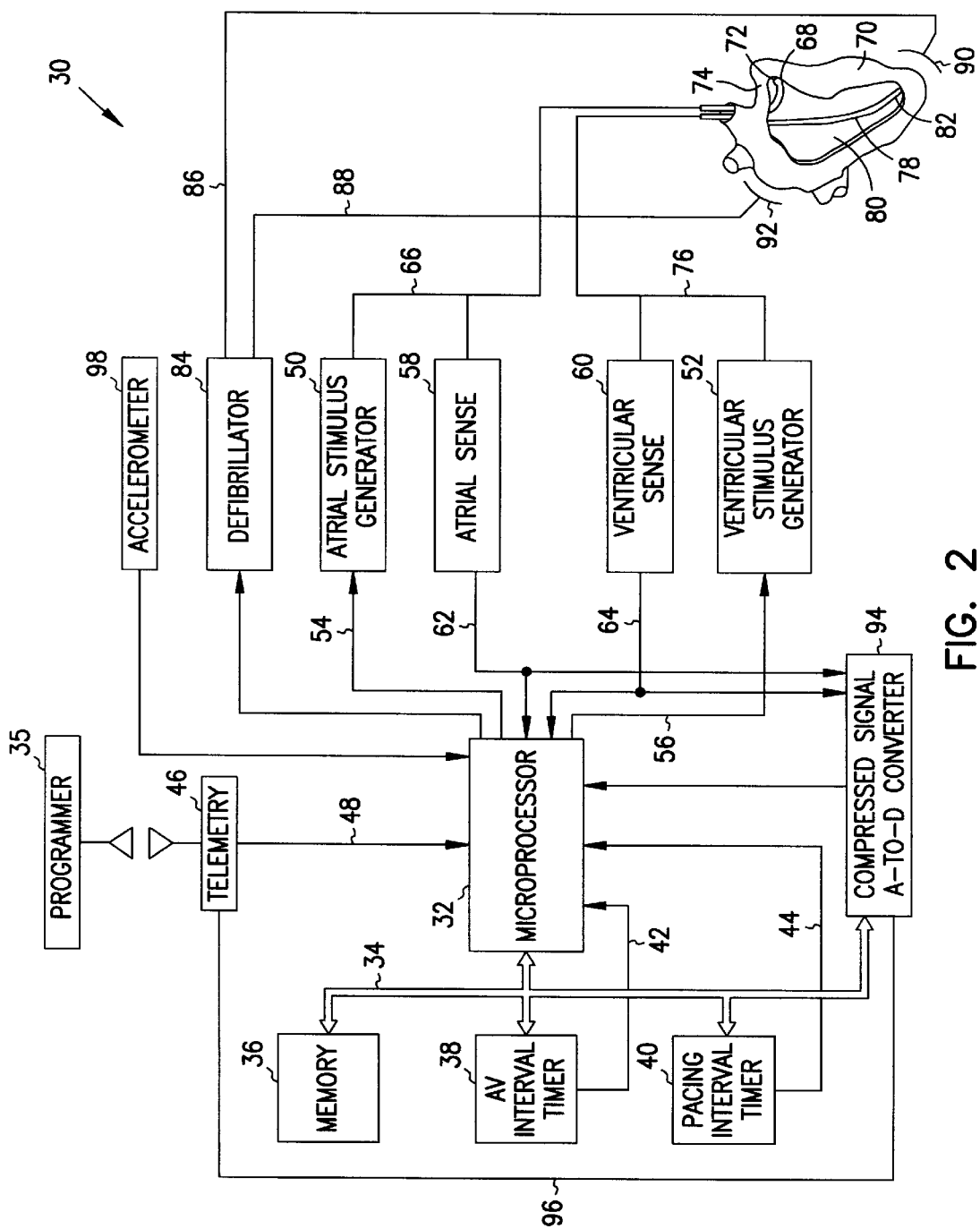
FIG. 2 illustrates a block diagram of an exemplary cardiac stimulator.

The cardiac stimulator 10 uses electronic circuitry to perform its functions, such as the circuitry illustrated in FIG. 2 and generally designated by the reference numeral 30. A microprocessor 32 provides pacemaker control and computational facilities. Although it will be appreciated that other forms of circuitry, such as analog or discrete digital circuitry, can be used in place of microprocessor 32, a microprocessor is typically advantageous due to its miniature size and its flexibility. A particularly energy efficient microprocessor, which is designed specifically for use in pacemakers, is fully described in U.S. Pat. Nos. 4,390,022 and 4,404,972.

The microprocessor 32 has input/output ports connected in a conventional manner via bidirectional bus 34 to memory 36, an AV interval timer 38, and a pacing interval timer 40. In addition, the AV interval timer 38 and pacing interval timer 40 each has an output connected to a corresponding input port of the microprocessor 32 by lines 42 and 44 respectively. Memory 36 may include both ROM and RAM, and the microprocessor 32 may also contain additional ROM and RAM. The pacemaker operating routine is typically stored in ROM, while the RAM stores programmable parameters and variables in conjunction with the pacemaker operation.

The AV and pacing interval timers 38 and 40 may be external to the microprocessor 32, as illustrated, or internal thereto. The timers 38 and 40 may be, for instance, suitable conventional up/down counters of the type that are initially loaded with a count value and count up to or down from the value and output a roll-over bit upon completing the programmed count. The initial count value is loaded into the timers 38, 40 on bus 34 and the respective roll-over bits are output to the microprocessor 32 on lines 42 and 44.

The microprocessor 32 typically also has an input/output port connected to a telemetry interface 46 by line 48. The pacemaker, when implanted, is thus able to receive pacing and rate control parameters from an external programmer 35 and to send data to an external receiver if desired. Many suitable telemetry systems are known to those skilled in the art. One such system and encoding arrangement is described in U.S. Pat. No. 4,539,992.

The microprocessor output ports are connected to inputs of an atrial stimulus pulse generator 50 and a ventricular stimulus pulse generator 52 by control lines 54 and 56, respectively. The microprocessor 32 transmits pulse parameter data, such as amplitude and width, as well as enable/disable and pulse initiation codes to the generators 50, 52 on the respective control lines. The microprocessor 32 also has input ports connected to outputs of an atrial sense amplifier 58 and a ventricular sense amplifier 60 by lines 62 and 64 respectively. The atrial and ventricular sense amplifiers 58, 60 detect occurrences of P-waves and R-waves respectively.

The input of the atrial sense amplifier 58 and the output of the atrial stimulus pulse generator 50 are connected to a first conductor 66 which is inserted in a first conventional lead 68. Lead 68 is inserted into a heart 70 intravenously or in any other suitable manner. The lead 66 has an electrically conductive pacing/sensing tip 72 at its distal end which is electrically connected to the conductor 66. The pacing/sensing tip 72 is typically lodged in the right atrium 74.

The input of the ventricular sense amplifier 60 and the output of the ventricular stimulus pulse generator 52 are connected to a second conductor 76. The second conductor 76 is inserted in a second conventional lead 78 which is inserted intravenously or otherwise in the right ventricle 80 of the heart 70. The second lead 78 has an electrically conductive pacing/sensing tip 82 at its distal end. The pacing/sensing tip 82 is electrically connected to the conductor 76. The pacing/sensing tip 82 is typically lodged on the wall of the right ventricle.

The conductors 66 and 76 conduct the stimulus pulses generated by the atrial and ventricular stimulus pulse generators 50 and 52, respectively, to the pacing/sensing tips 72, 82. The pacing/sensing tips 72, 82 and corresponding conductors 66, 76 also conduct sensed cardiac electrical signals in the right atrium and right ventricle to the atrial and ventricular sense amplifiers 58, 60.

In addition, it may be desired to provide defibrillation capability in the cardiac stimulator 10. If this is the case, a high voltage defibrillator circuit 84 is provided which is controlled by the microprocessor 32. The defibrillator circuit 84 is connected to heart tissue through two high voltage leads 86, 88 which communicate with the heart through electrodes 90, 92. In the illustrated embodiment, epicardial patch electrodes are diagrammatically represented. However, other electrode configurations, including endocardial electrodes, may also be suitable.

The atrial and ventricular sense amplifiers 58, 60 communicate both with the microprocessor and with a compressed signal A-to-D converter 94. The compressed signal A-to-D converter 94 communicates through the bus 34 with memory 36 and the microprocessor 32, primarily, and on a line 96 with the telemetry 46. Thus, the output of the converter 94 can be manipulated by the microprocessor 32, or stored in memory 36 or directly communicated through the telemetry 46 to the programmer 35. The stored output of the converter 94 may also be subsequently communicated from memory 36 through the telemetry 46 to the programmer 35.

The microprocessor 32 may also base its control on other parameters, such as information received from other sensors. For example, an activity sensor 98, such as an implanted accelerometer, may be used to gather information relating to changing environmental or physiological conditions. Although the use of an accelerometer as the activity sensor 98 may be advantageous, other types of sensors may also be used to gauge certain types of physical activity or physical condition, such as vibration sensors, temperature sensors, oxygen sensors, pH sensors, and/or impedance sensors. Indeed, when the dual-chamber cardiac stimulator 10 is operating in rate-responsive mode, the stimulator 10 typically adjusts the pacing rate in response to one or more detected physiological or environmental parameters correlated to a physiologic need.

One method by which the microprocessor 32 may control the cardiac stimulator 10 is illustrated in FIGS. 3–6. As mentioned above, certain techniques for controlling cardiac stimulators have used a fixed VPRP which is limited by the maximum pacing rate so that the VPRP must be shorter than the shortest possible pacing interval. As a result, the fixed VPRP may not be ideal for slow pacing rates. Also, certain techniques for controlling cardiac stimulators have linearly adjusted the VPRP between two limits imposed by the maximum pacing rate and the minimum pacing rate. However, using such a technique, a situation may exist where the VPRP may extend beyond the PVARP, thus possibly leading to a condition where ventricular pacing may occur during a vulnerable period in the ventricle. The technique disclosed in the flow chart 100 of FIG. 3 addresses the shortcomings of previous techniques by holding the PVARP interval steady while dynamically adjusting the VPRP until the VPRP reaches a certain limit, such as the interval of the programmed PVARP. At that limit, the VPRP and PVARP are both dynamically adjusted.

Figure 3:
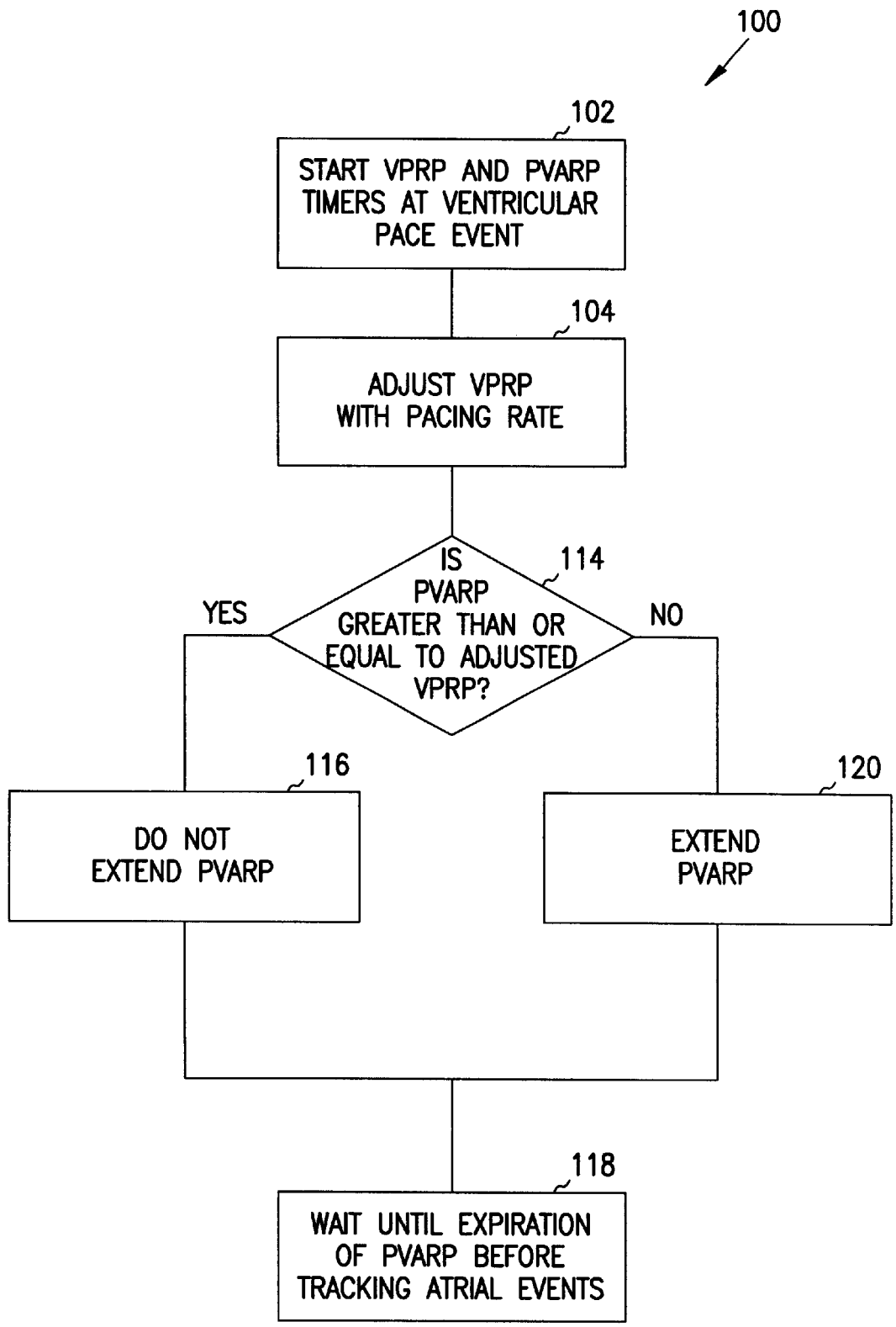
FIG. 3 illustrates a flowchart depicting a method by which the cardiac stimulator adjusts PVARP and VPRP during operation.
Figure 4:
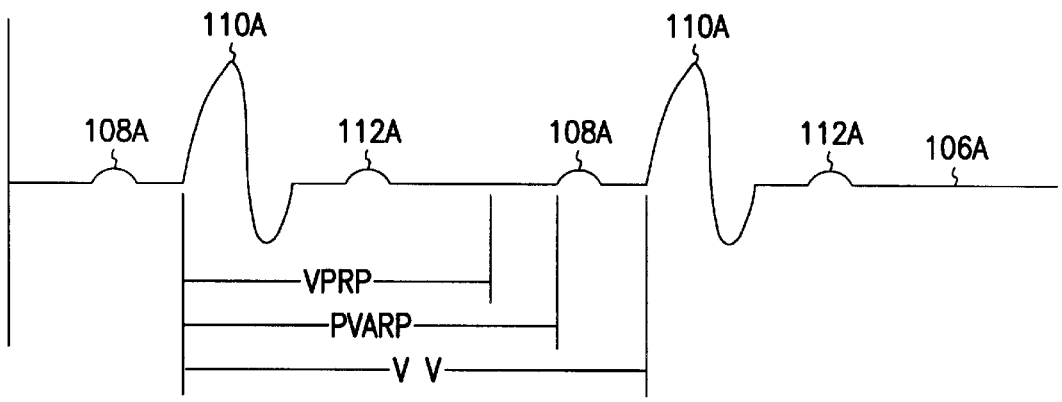
FIG. 4 illustrates an exemplary electrocardiogram during fast pacing, with periods being labeled to depict the operation of the cardiac stimulator as set forth in FIG. 3.
Figure 5:
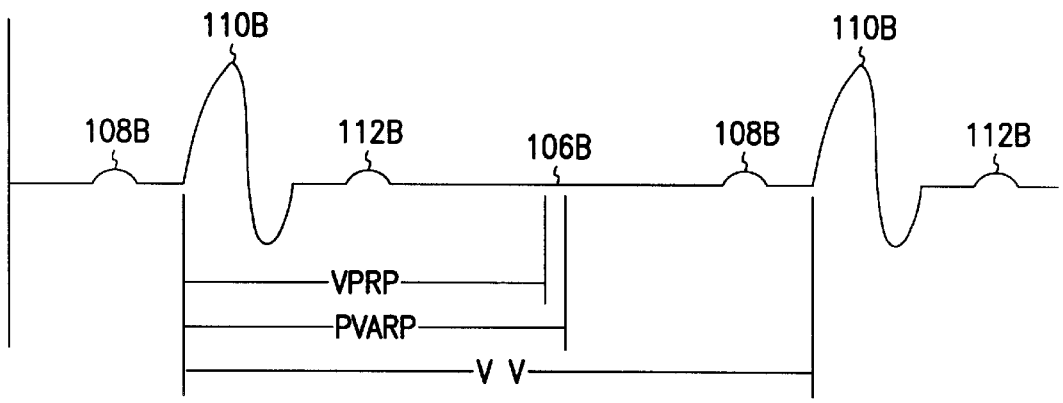
FIG. 5 illustrates an exemplary electrocardiogram during moderate pacing, with periods being labeled to depict the operation of the cardiac stimulator as set forth in FIG. 3.
Figure 6:
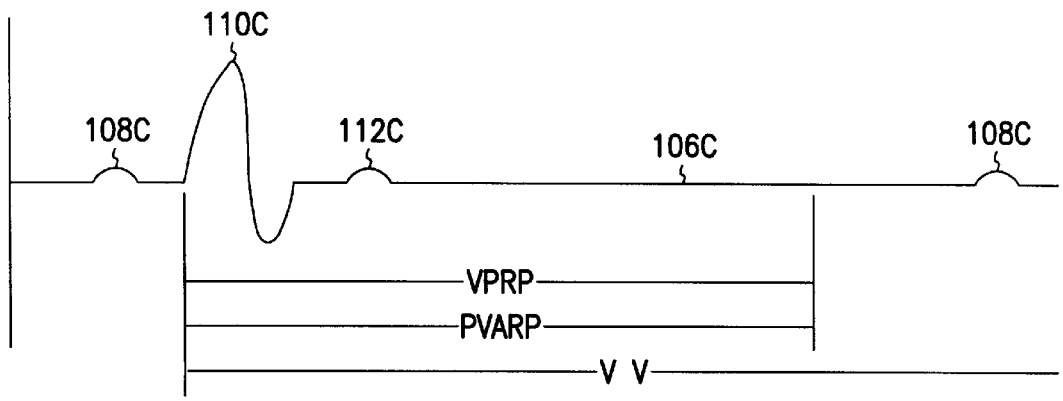
FIG. 6 illustrates an exemplary electrocardiogram during slow pacing, with periods being labeled to depict the operation of the cardiac stimulator as set forth in FIG. 3.

To gain a better understanding of the technique in the flowchart 100 of FIG. 3, the manner in which the VPRP and the PVARP are adjusted is illustrated in the three examples of FIGS. 4–6. FIGS. 4–6 illustrate these periods during fast pacing, moderate pacing, and slow pacing, respectively. When a ventricular pace event occurs, i.e., at the beginning of each V—V pacing interval, timers are started for the PVARP and VPRP intervals. (Block 102). As the pacing rate changes, the VPRP is adjusted in accordance with the pacing rate. (Block 104). Either a linear or non-linear adjustment may be employed.

By referring to FIG. 4, it can be seen that the electrocardiogram 106A illustrates heartbeats, which are characterized by an atrial P-wave 108A, a ventricular QRS-wave 110A, and a ventricular repolarization T-wave 112A, that are relatively close together, thus indicating a relatively fast pacing rate. For the purposes of this discussion, we will assume that the electrocardiogram 106A represents the maximum pacing rate of the cardiac stimulator 10. In this situation, the PVARP is set at a fixed interval so that it extends from the beginning of the V—V interval and ends just prior to the next expected atrial P-wave 108A. Similarly, the VPRP is set at its minimum interval which begins at the beginning of the V—V pacing interval and ends prior to the end of the PVARP.

As the pacing rate slows, the VPRP is adjusted upwardly. For instance, as illustrated in FIG. 5, the electrocardiogram 106B depicts heartbeats, which are characterized by the atrial P-waves 108B, the ventricular QRS-waves 110B, and the ventricular repolarization T-waves 112B, that are spaced farther apart, thus indicating a more moderate pacing rate. As a result, it should be noted that the VPRP is greater. In fact, in this example it is almost as great as the PVARP which remains unchanged.

Referring again to FIG. 3, during each pacing interval, the programmed PVARP is compared with the current VPRP to determine whether the PVARP is greater than or equal to the VPRP. (Block 114). If the PVARP is greater than or equal to the current VPRP, as in FIGS. 4 and 5, the PVARP is not extended. (Block 116). Thus, the microprocessor 32 waits until the expiration of the PVARP before tracking atrial events. (Block 118).

However, as the pacing rate slows even further and the VPRP continues to become greater, the current VPRP will ultimately become greater than or equal to the programmed PVARP. In this situation, the PVARP is extended to be equal to or greater than the current VPRP. (Block 120). An example of this situation is illustrated in FIG. 6. The electrocardiogram 106C depicts heartbeats, which are characterized by the atrial P-waves 108C, the ventricular QRS-waves 110C, and the ventricular repolarization T-waves 112C, that are spaced farther apart than those illustrated in FIGS. 4 and 5, thus indicating a slower pacing rate. In fact, the pacing rate is so slow that the VPRP has been extended past the programmed PVARP illustrated in FIGS. 4 and 5. However, using the technique depicted in the flowchart 100, the PVARP has been similarly extended to be equal to the VPRP in this example.

The adjustments described above may be depicted by the equations set forth below.

$$VPRP = f_1(\text{pacing rate})$$

$$PVARP = f_2(\text{pacing rate})$$

$$f_1(\text{pacing rate}) = r_{base} - [(i_{base} - i_{rate}) * (r_{base} - r_{max})]/(i_{base} - i_{max})$$

$f_2$(pacing rate) = the larger of programmed PVARP setting or VPRP duration where $r_{base}$=desired VPRP for the baseline bradycardia pacing rate (lower rate)

$r_{max}$=desired VPRP for the maximum pacing rate (upper rate)

$i_{base}$=interval of the baseline bradycardia pacing rate (lower rate)

$i_{max}$=interval of the maximum pacing rate (upper rate)

$i_{rate}$=interval of the current pacing rate

Another method by which the microprocessor 32 may control the cardiac stimulator 10 is illustrated in FIGS. 7–10. The technique disclosed in FIGS. 3–6 holds the PVARP interval steady while dynamically adjusting the VPRP until the VPRP reaches a limit at which the VPRP and PVARP are both dynamically adjusted. In contrast, the technique disclosed in FIGS. 7–10 dynamically adjusts both the VPRP and PVARP with the pacing rate throughout the pacing range of the cardiac stimulator 10.

Figure 7:
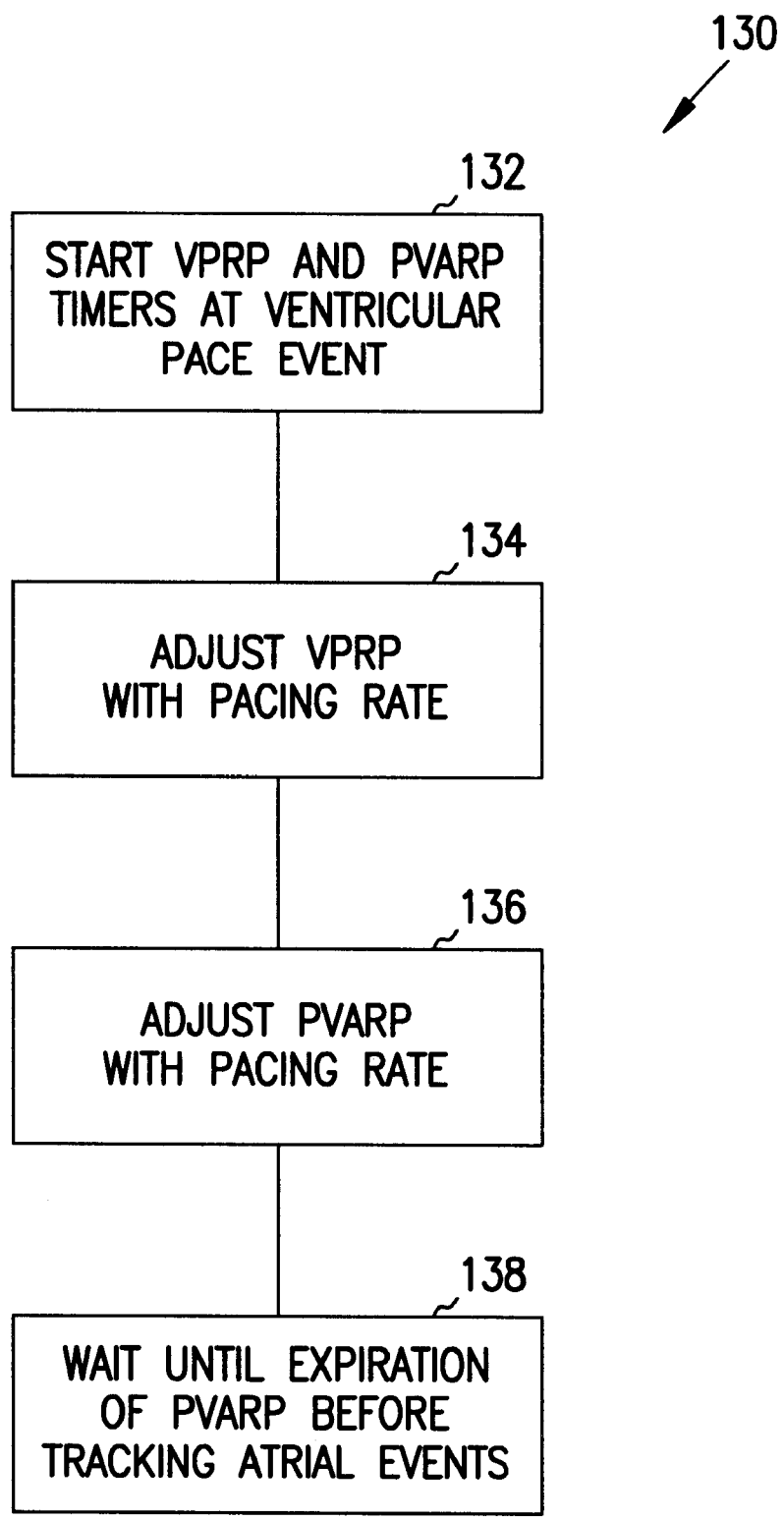
FIG. 7 illustrates a flowchart depicting an alternative method by which the cardiac stimulator adjusts PVARP and VPRP during operation.
Figure 8:
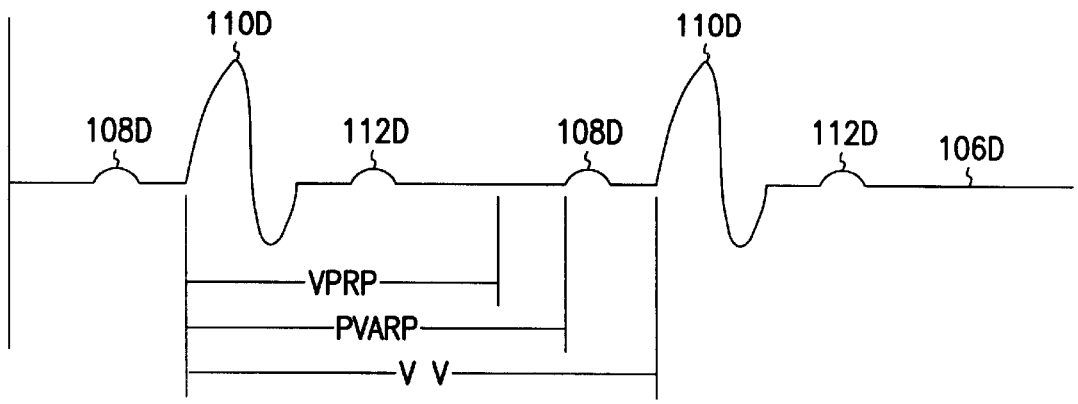
FIG. 8 illustrates an exemplary electrocardiogram during fast pacing, with periods being labeled to depict the operation of the cardiac stimulator as set forth in FIG. 7.
Figure 9:
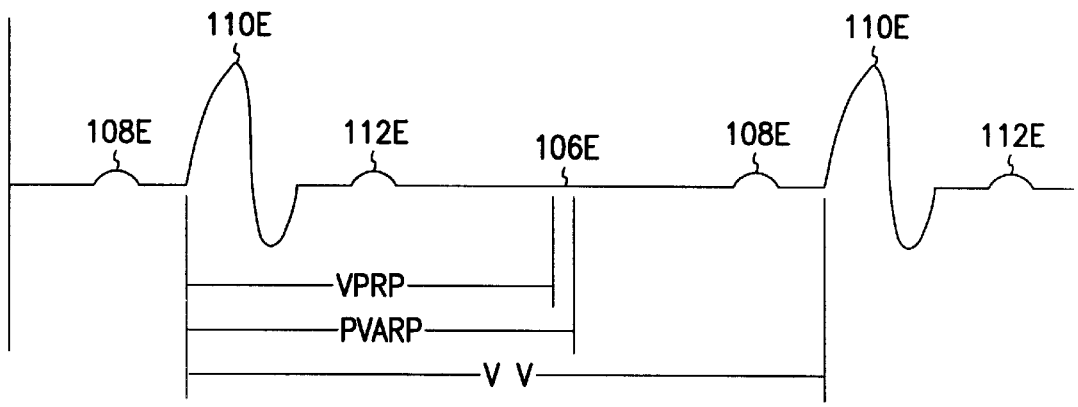
FIG. 9 illustrates an exemplary electrocardiogram during moderate pacing, with periods being labeled to depict the operation of the cardiac stimulator as set forth in FIG. 7.
Figure 10:
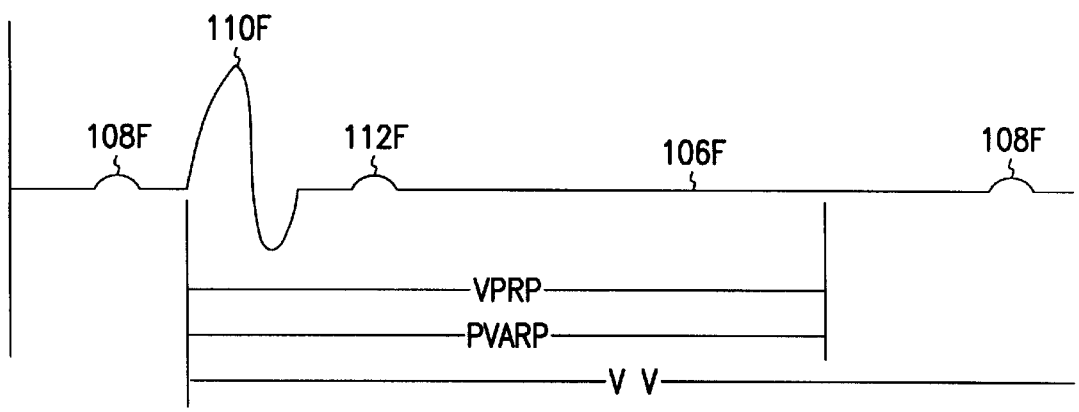
FIG. 10 illustrates an exemplary electrocardiogram during slow pacing, with periods being labeled to depict the operation of the cardiac stimulator as set forth in FIG. 7.

To gain a better understanding of the technique illustrated in the flowchart 130 of FIG. 7, the manner in which the VPRP and the PVARP are adjusted is illustrated in the three examples of FIGS. 8–10. FIGS. 8–10 illustrate these periods during fast pacing, moderate pacing, and slow pacing, respectively. When a ventricular pace event occurs, i.e., at the beginning of each V—V pacing interval, timers are started for the PVARP and VPRP intervals. (Block 132). As the pacing rate changes, the VPRP and the PVARP may be adjusted in accordance with the pacing rate, although the PVARP may be adjusted in accordance with the VPRP instead. (Blocks 134 and 136). Either a linear or non-linear adjustment may be employed, and it should be understood that the VPRP and PVARP need not be adjusted in the same manner so long as the PVARP remains greater than or equal to the VPRP. After these adjustments, the microprocessor 32 waits until the expiration of the PVARP before tracking atrial events. (Block 138).

By referring to FIG. 8, it can be seen that the electrocardiogram 106D illustrates heartbeats, which are characterized by an atrial P-wave 108D, a ventricular QRS-wave 110D, and a ventricular repolarization T-wave 112D, that are relatively close together, thus indicating a relatively fast pacing rate. For the purposes of this discussion, we will assume that the electrocardiogram 106D represents the maximum pacing rate of the cardiac stimulator 10. In this situation, the PVARP is set at a minimum interval so that it extends from the beginning of the V—V interval and ends just prior to the next expected atrial P-wave 108D. Similarly, the VPRP is set at its minimum interval which begins at the beginning of the V—V pacing interval and ends prior to the end of the PVARP.

As the pacing rate slows, the VPRP and PVARP are adjusted upwardly. For instance, as illustrated in FIG. 9, the electrocardiogram 106E depicts heartbeats, which are characterized by the atrial P-waves 108E, the ventricular QRS-waves 110E, and the ventricular repolarization T-waves 112E, that are spaced farther apart, thus indicating a more moderate pacing rate. As a result, it should be noted that both the VPRP and PVARP are greater.

As the pacing rate slows even further and the VPRP and PVARP continue to increase until one or both reaches a maximum limit determined by the minimum pacing rate. An example of this situation is illustrated in FIG. 10. The electrocardiogram 106F depicts heartbeats, which are characterized by the atrial P-waves 108F, the ventricular QRS-waves 110F, and the ventricular repolarization T-waves 112F, that are spaced farther apart than those illustrated in FIGS. 8 and 9, thus indicating a slower pacing rate. Accordingly, both the VPRP and PVARP have been extended further as well in accordance with the slower pacing rate.

As can be seen by the examples discussed above, these techniques allow PVARP extensions so that the PVARP may be set to a suitably low physiologic value with the comfort of knowing that the PVARP will be extended whenever slower pacing rates extend the VPRP. Thus, atrial tracking and ventricular inhibition during a preceding VPRP is prevented. Furthermore, the extension of the PVARP at slower pacing rates provided better prevention of tracking of spurious premature atrial events (PAEs) and sudden-onset atrial arrhythmias. In contrast, slow-onset rate increases, such as those brought on by exercise, will be tracked, and the subsequent increase in the pacing rate will further decrease PVARP to its minimum value as the VPRP decreases.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A cardiac stimulator comprising:
a sensing circuit adapted to sense a condition of a heart and adapted to deliver electrical stimulation to the heart; and
a control circuit coupled to the sensing circuit, the control circuit adjusting a ventricular refractory period (VRP) correlative to a pacing rate and adjusting a post-ventricular atrial refractory period (PVARP) correlative to the VRP.

2. The cardiac stimulator, as set forth in claim 1, wherein the PVARP is adjusted to be greater than or equal to the VRP.

3. The cardiac stimulator, as set forth in claim 1, wherein the PVARP remains at an initial value until the VRP equals or exceeds the PVARP.

4. The cardiac stimulator, as set forth in claim 1, wherein the PVARP is adjusted correlative to the pacing rate.

5. The cardiac stimulator, as set forth in claim 1, wherein the VRP is adjusted linearly.

6. The cardiac stimulator, as set forth in claim 1, wherein the PVARP is adjusted linearly.

7. The cardiac stimulator, as set forth in claim 1, wherein the VRP is adjusted non-linearly.

8. The cardiac stimulator, as set forth in claim 1, wherein the PVARP is adjusted non-linearly.

9. The cardiac stimulator, as set forth in claim 1, wherein the control circuit delays electrical stimulation delivered by the sensing circuit until after the PVARP.

10. A cardiac stimulator comprising:
a sensing circuit adapted to sense a condition of a heart and adapted to deliver electrical stimulation to the heart; and
a control circuit coupled to the sensing circuit, the control circuit adjusting a ventricular refractory period (VRP) correlative to a pacing rate and adjusting a post-ventricular atrial refractory period (PVARP) correlative to the pacing rate.

11. The cardiac stimulator, as set forth in claim 10, wherein the PVARP is adjusted to be greater than or equal to the VRP.

12. The cardiac stimulator, as set forth in claim 10, wherein the VRP is adjusted linearly.

13. The cardiac stimulator, as set forth in claim 10, wherein the PVARP is adjusted linearly.

14. The cardiac stimulator, as set forth in claim 10, wherein the VRP is adjusted non-linearly.

15. The cardiac stimulator, as set forth in claim 10, wherein the PVARP is adjusted non-linearly.

16. The cardiac stimulator, as set forth in claim 10, wherein the control circuit delays electrical stimulation delivered by the sensing circuit until after the PVARP.

17. A cardiac stimulator comprising:
   a sensing circuit adapted to sense a condition of a heart and adapted to deliver electrical stimulation to the heart; and
   a control circuit coupled to the sensing circuit, the control circuit executing an algorithm for controlling the sensing circuit, the algorithm:
      adjusting a ventricular refractory period (VRP) correlative to a pacing rate; and
      adjusting a post-ventricular atrial refractory period (PVARP) to be greater than or equal to the VRP.

18. The cardiac stimulator, as set forth in claim 17, wherein the PVARP remains at an initial value until the VRP equals or exceeds the PVARP.

19. The cardiac stimulator, as set forth in claim 17, wherein the PVARP is adjusted correlative to the pacing rate.

20. The cardiac stimulator, as set forth in claim 17, wherein the PVARP is adjusted correlative to the VRP.

21. The cardiac stimulator, as set forth in claim 20, the algorithm:
   comparing the VRP with the PVARP; and
   if the comparison indicates that VRP is greater than the PVARP, extending the PVARP to be greater than or equal to the VRP.

22. The cardiac stimulator, as set forth in claim 17, wherein the VRP is adjusted linearly.

23. The cardiac stimulator, as set forth in claim 17, wherein the PVARP is adjusted linearly.

24. The cardiac stimulator, as set forth in claim 17, wherein the VRP is adjusted non-linearly.

25. The cardiac stimulator, as set forth in claim 17, wherein the PVARP is adjusted non-linearly.

26. The cardiac stimulator, as set forth in claim 17, wherein the control circuit delays electrical stimulation delivered by the sensing circuit until after the PVARP.

27. A cardiac stimulator comprising:
   a sensing circuit adapted to deliver a signal correlative to a ventricular pace event; and
   a control circuit coupled to the sensing circuit to receive the signal delivered by the sensing circuit, the control circuit executing an algorithm for controlling the cardiac stimulator, the algorithm:
      starting a post-ventricular atrial refractory period (PVARP) in response to the ventricular pace event;
      starting a ventricular refractory period (VRP) in response to the ventricular pace event;
      adjusting the VRP correlative to a pacing rate;
      comparing the PVARP to the VRP; and
      if the PVARP is less than the VRP, adjusting the PVARP to be greater than or equal to the VRP.

28. The cardiac stimulator, as set forth in claim 27, wherein the VRP is adjusted linearly.

29. The cardiac stimulator, as set forth in claim 27, wherein the PVARP is adjusted linearly.

30. The cardiac stimulator, as set forth in claim 27, wherein the VRP is adjusted non-linearly.

31. The cardiac stimulator, as set forth in claim 27, wherein the PVARP is adjusted non-linearly.

32. A cardiac stimulator comprising:
   means for determining a pacing rate of the cardiac stimulator;
   means for adjusting a ventricular refractory period (VRP) correlative to the pacing rate; and
   means for adjusting a post-ventricular atrial refractory period (PVARP) correlative to the VRP.

33. The cardiac stimulator, as set forth in claim 32, wherein the VRP adjusting means comprises:
   means for adjusting the VRP linearly.

34. The cardiac stimulator, as set forth in claim 32, wherein the VRP adjusting means comprises:
   means for adjusting the VRP non-linearly.

35. The cardiac stimulator, as set forth in claim 32, wherein the PVARP adjusting means comprises:
   means for adjusting the PVARP linearly.

36. The cardiac stimulator, as set forth in claim 32, wherein the PVARP adjusting means comprises:
   means for adjusting the PVARP non-linearly.

37. The cardiac stimulator, as set forth in claim 32, wherein the PVARP adjusting means comprises:
   means for comparing the VRP to the PVARP; and
   means for adjusting the PVARP to be greater than or equal to the VRP.

38. A cardiac stimulator comprising:
   means for determining a pacing rate of the cardiac stimulator;
   means for adjusting a ventricular refractory period (VRP) correlative to the pacing rate; and
   means for adjusting a post-ventricular atrial refractory period (PVARP) correlative to the pacing rate.

39. The cardiac stimulator, as set forth in claim 38, wherein the VRP adjusting means comprises:
   means for adjusting the VRP linearly.

40. The cardiac stimulator, as set forth in claim 38, wherein the VRP adjusting means comprises:
   means for adjusting the VRP non-linearly.

41. The cardiac stimulator, as set forth in claim 38, wherein the PVARP adjusting means comprises:
   means for adjusting the PVARP linearly.

42. The cardiac stimulator, as set forth in claim 38, wherein the PVARP adjusting means comprises:
   means for adjusting the PVARP non-linearly.

43. The cardiac stimulator, as set forth in claim 38, wherein the PVARP adjusting means comprises:
   means for adjusting the PVARP to be greater than or equal to the VRP.

44. A tangible medium comprising a computer algorithm, the computer algorithm performing the acts of:
   adjusting a ventricular refractory period (VRP) of a cardiac stimulator correlative to a pacing rate of the cardiac stimulator, and
   adjusting a post-ventricular atrial refractory period (PVARP) of the cardiac stimulator to be greater than or equal to the VRP.

45. The tangible medium, as set forth in claim 44, wherein the algorithm performs the acts of:
   starting the PVARP in response to a ventricular pace event; and
   starting the VPRP in response to the ventricular pace event.

46. The tangible medium, as set forth in claim 44, wherein the algorithm performs the acts of:

comparing the PVARP to the VRP; and if the PVARP is less than the VRP, adjusting the PVARP to be greater than or equal to the VRP.

47. The tangible medium, as set forth in claim 44, wherein the algorithm performs the act of:

linearly adjusting the VRP.

48. The tangible medium, as set forth in claim 44, wherein the algorithm performs the act of:

non-linearly adjusting the VRP.

49. The tangible medium, as set forth in claim 44, wherein the algorithm performs the act of:

linearly adjusting the PVARP.

50. The tangible medium, as set forth in claim 44, wherein the algorithm performs the act of:

non-linearly adjusting the PVARP.

51. The tangible medium, as set forth in claim 44, wherein the algorithm performs the act of:

adjusting the PVARP correlative to the pacing rate.

52. The tangible medium, as set forth in claim 44, wherein the algorithm performs the act of:

adjusting the PVARP correlative to the VRP.

53. A method of operating a cardiac stimulator comprising the acts of:

determining a pacing rate;

adjusting a ventricular refractory period (VRP) correlative to the pacing rate; and adjusting a post-ventricular atrial refractory period (PVARP) correlative to the VRP.

54. A method of operating a cardiac stimulator comprising the acts of:

adjusting a ventricular refractory period (VRP) correlative to a pacing rate; and adjusting a post-ventricular atrial refractory period (VARP) to be greater than or equal to the VRP.

* * * * *

UNITED STATES PATENT AND TRADEMARK OFFICE
CERTIFICATE OF CORRECTION

PATENT NO.     : 6,282,447 B1
DATED          : August 28, 2001
INVENTOR(S)    : Douglas J. Cook, Randolph K. Armstrong, Joseph W. Vandegriff and Denise R. Brown It is certified that error appears in the above-identified patent and that said Letters Patent is hereby corrected as shown below:

<u>Column 16,</u>
Line 17, delete "(VARP)" and insert -- (PVARP) --, therefor.

Signed and Sealed this

Fourth Day of June, 2002

Attest:

JAMES E. ROGAN
*Attesting Officer*   *Director of the United States Patent and Trademark Office*